(12) United States Patent
Rochetin

(10) Patent No.: US 7,544,211 B2
(45) Date of Patent: Jun. 9, 2009

(54) OFFSET STEM TIBIAL IMPLANT

(75) Inventor: Olivier Rochetin, Marcilly le Chatel (FR)

(73) Assignee: Tornier, Saint-Ismier (FR)

( * ) Notice: Subject to any disclaimer, the term of this patent is extended or adjusted under 35 U.S.C. 154(b) by 113 days.

(21) Appl. No.: 11/670,274

(22) Filed: Feb. 1, 2007

(65) Prior Publication Data

US 2007/0179628 A1   Aug. 2, 2007

(30) Foreign Application Priority Data

Feb. 1, 2006   (FR)   .................................. 06 00913

(51) Int. Cl.
  *A61F 2/36*   (2006.01)
(52) U.S. Cl. ................. 623/20.34; 623/20.15
(58) Field of Classification Search .............. 623/20.14, 623/20.15, 20.21, 20.22, 20.24, 20.28, 20.31, 623/20.32, 20.34
See application file for complete search history.

(56) References Cited

U.S. PATENT DOCUMENTS

| | | | |
|---|---|---|---|
| 4,219,893 A | 9/1980 | Noiles | |
| 4,301,553 A | 11/1981 | Noiles | |
| 4,538,305 A | 9/1985 | Englebrecht et al. | |
| 4,624,673 A | 11/1986 | Meyer | |
| 4,634,444 A | 1/1987 | Noiles | |
| 4,822,366 A | 4/1989 | Bolesky | |
| 4,846,839 A | 7/1989 | Noiles | |
| 4,888,021 A | 12/1989 | Forte et al. | |

(Continued)

FOREIGN PATENT DOCUMENTS

EP   0993813   4/2000

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner*—David Isabella
*Assistant Examiner*—Yashita Sharma
(74) *Attorney, Agent, or Firm*—Faegre & Benson, LLP

(57) ABSTRACT

A low-profile offset stem tibial implant includes a tray with a plate that extends transversely around a first tibial axis. The plate includes a distal surface adapted to engage against the prepared surface of the tibia. An engagement portion extends away from the distal surface of the plate substantially along the first tibial axis. A stem is provided with a distal end adapted to be introduced into the medullary canal of the tibia along a second tibial axis and a proximal end. One or more adapter elements are provided with a proximal portion sized to engage with the engagement portion of the plate along the first tibial axis. The adapter element also includes a distal portion adapted to engage with the proximal end of the stem along the second tibial axis. The adapter element permits adjustment of the medio-lateral and antero-posterior position of the second tibial axis relative to the first tibial axis. A plurality of indexing features are located at an interface between the plate and the adapter element to secure the tray in at least three discrete locations around the first tibial axis when in an assembled configuration.

35 Claims, 3 Drawing Sheets

U.S. PATENT DOCUMENTS

| | | | |
|---|---|---|---|
| 4,904,110 | A | 2/1990 | Klein |
| 4,936,853 | A | 6/1990 | Fabian et al. |
| 4,938,769 | A | 7/1990 | Shaw |
| 4,944,757 | A | 7/1990 | Martinez et al. |
| 4,950,297 | A | 8/1990 | Elloy et al. |
| 4,985,037 | A | 1/1991 | Petersen |
| 5,002,581 | A | 3/1991 | Paxson et al. |
| 5,011,496 | A | 4/1991 | Forte et al. |
| 5,127,914 | A | 7/1992 | Calderale et al. |
| 5,133,760 | A | 7/1992 | Petersen et al. |
| 5,152,796 | A | 10/1992 | Slamin |
| 5,171,289 | A | 12/1992 | Tornier |
| 5,194,066 | A | 3/1993 | Van Zile |
| 5,226,915 | A | 7/1993 | Bertin |
| 5,271,737 | A | 12/1993 | Baldwin et al. |
| 5,290,313 | A | 3/1994 | Heldreth |
| 5,314,485 | A | 5/1994 | Judet |
| 5,326,359 | A | 7/1994 | Oudard |
| 5,330,534 | A | 7/1994 | Herrington et al. |
| 5,336,225 | A | 8/1994 | Zang |
| 5,358,526 | A | 10/1994 | Tornier |
| 5,405,399 | A | 4/1995 | Tornier |
| 5,429,639 | A | 7/1995 | Judet |
| 5,458,650 | A | 10/1995 | Carrett et al. |
| 5,505,731 | A | 4/1996 | Tornier |
| 5,507,824 | A | 4/1996 | Lennox |
| 5,545,228 | A | 8/1996 | Kambin |
| 5,556,433 | A | 9/1996 | Gabriel et al. |
| 5,591,168 | A | 1/1997 | Judet et al. |
| 5,613,970 | A * | 3/1997 | Houston et al. ............... 606/88 |
| 5,662,651 | A | 9/1997 | Tornier et al. |
| 5,676,702 | A | 10/1997 | Ratron |
| 5,683,472 | A | 11/1997 | O'Neil et al. |
| 5,702,447 | A | 12/1997 | Walch et al. |
| 5,702,457 | A | 12/1997 | Walch et al. |
| 5,702,478 | A | 12/1997 | Tornier |
| 5,766,256 | A | 6/1998 | Oudard et al. |
| 5,776,200 | A | 7/1998 | Johnson et al. |
| 5,782,920 | A * | 7/1998 | Colleran ................. 623/20.34 |
| 5,782,921 | A | 7/1998 | Colleran et al. |
| 5,824,106 | A | 10/1998 | Fournol |
| 5,879,391 | A | 3/1999 | Slamin |
| 5,879,395 | A | 3/1999 | Tornier et al. |
| 5,944,756 | A | 8/1999 | Fischetti et al. |
| 6,146,424 | A | 11/2000 | Gray, Jr. et al. |
| 6,162,254 | A | 12/2000 | Timoteo |
| 6,162,255 | A | 12/2000 | Oyola |
| 6,165,224 | A | 12/2000 | Tornier |
| 6,168,629 | B1 | 1/2001 | Timoteo |
| 6,171,341 | B1 | 1/2001 | Boileau et al. |
| 6,183,519 | B1 | 2/2001 | Bonnin et al. |
| 6,206,925 | B1 | 3/2001 | Tornier |
| 6,214,052 | B1 | 4/2001 | Burkinshaw |
| 6,299,646 | B1 | 10/2001 | Chambat et al. |
| 6,328,758 | B1 | 12/2001 | Tornier et al. |
| 6,334,874 | B1 | 1/2002 | Tornier et al. |
| 6,379,387 | B1 | 4/2002 | Tornier |
| 6,454,809 | B1 | 9/2002 | Tornier |
| 6,488,712 | B1 | 12/2002 | Tornier et al. |
| 6,540,770 | B1 | 4/2003 | Tornier et al. |
| 6,582,469 | B1 | 6/2003 | Tornier |
| 6,599,295 | B1 | 7/2003 | Tornier et al. |
| 6,626,946 | B1 | 9/2003 | Walch et al. |
| 6,761,740 | B2 | 7/2004 | Tornier |
| 6,767,368 | B2 | 7/2004 | Tornier |
| 6,802,864 | B2 | 10/2004 | Tornier |
| 6,824,567 | B2 | 11/2004 | Tornier et al. |
| 6,890,357 | B2 | 5/2005 | Tornier |
| 6,953,479 | B2 | 10/2005 | Carson et al. |
| 6,969,406 | B2 | 11/2005 | Tornier |
| 7,033,396 | B2 | 4/2006 | Tornier |
| 2003/0009170 | A1 | 1/2003 | Tornier |
| 2003/0009171 | A1 | 1/2003 | Tornier |
| 2003/0014120 | A1 | 1/2003 | Carson et al. |
| 2003/0028198 | A1 | 2/2003 | Tornier et al. |
| 2004/0134821 | A1 | 7/2004 | Tornier |
| 2004/0210220 | A1 | 10/2004 | Tornier |
| 2004/0215200 | A1 | 10/2004 | Tornier et al. |
| 2004/0230197 | A1 | 11/2004 | Tornier et al. |
| 2005/0010301 | A1 * | 1/2005 | Disilvestro et al. ....... 623/18.12 |
| 2005/0049709 | A1 | 3/2005 | Tornier |
| 2005/0055102 | A1 | 3/2005 | Tornier et al. |
| 2005/0165490 | A1 | 7/2005 | Tornier |
| 2005/0203536 | A1 | 9/2005 | Laffargue et al. |
| 2005/0278030 | A1 | 12/2005 | Tornier et al. |
| 2005/0278031 | A1 | 12/2005 | Tornier et al. |
| 2005/0278032 | A1 | 12/2005 | Tornier et al. |
| 2005/0278033 | A1 | 12/2005 | Tornier et al. |
| 2005/0288791 | A1 | 12/2005 | Tornier et al. |
| 2006/0015185 | A1 | 1/2006 | Chambat et al. |
| 2006/0173457 | A1 | 8/2006 | Tornier |
| 2006/0235538 | A1 | 10/2006 | Rochetin et al. |

FOREIGN PATENT DOCUMENTS

| | | |
|---|---|---|
| EP | 0853930 | 7/2002 |

OTHER PUBLICATIONS

Rochetin et al., U.S. Appl. No. 11/401,415, entitled "Surgical Apparatus for Implantation of a Partial or Total Knee Prosthesis," filed Apr. 11, 2006.

Ratron et al., U.S. Appl. No. 11/626,735, entitled "Surgical Instrumentation Kit for Inserting an Ankle Prothesis," filed Jan. 24, 2007.

* cited by examiner

OFFSET STEM TIBIAL IMPLANT

CROSS-REFERENCE TO RELATED APPLICATIONS

The present application claims priority to prior French Application No. 0600913, filed Feb. 1, 2006, the entire specification of which is hereby incorporated by reference.

FIELD OF THE INVENTION

The present invention relates to an offset stem tibial implant that includes a stem adapted to be introduced into the medullary canal of the tibia and a tray adapted to be fixed to the upper end of the tibia. One or more adapter elements are used to offset the tray relative to a longitudinal axis of the stem. The low profile of the present offset stem tibial implant provides a number of advantages over the prior art.

BACKGROUND OF THE INVENTION

Tibial implants generally form part of a knee prosthesis and are typically associated with a femoral implant fixed to the lower end of the femur. A pad is on the tray of the tibial implant and articulated against the femoral implant. The pad can either be fixed or mobile relative to the tray.

The use of an offset stem tibial implant aims to optimize the medio-lateral and antero-posterior positioning of the tray relative to the tibial medullary canal. The medullary canal dictates the position of the stem of the implant. Depending on the knee being operated upon, it is often desirable that the longitudinal axis of the stem and the centre axis of the tray are parallel, but offset, relative to one another. The offset can in practice be several millimetres.

Many tibial implants currently have an offset stem attached to the distal end of a pin of the tray. For example, the distal end of an extension of lengthened material extends over the centre axis of the tray from the distal face of the tray and is introduced into the epiphyseal end of the medullary canal of the tibia. The length of these pins generally extends over 20 to 40 millimeters (mm), depending on the implants. Consequently, the interface between the stem and the pin is located further into the medullary canal than is desirable.

To offset the axis of the stem relative to that of the pin, the proximal part of the stem has an angled shape so that its proximal end is offset relative to its distal part received in the diaphyseal part of the medullary canal, as proposed in U.S. Pat. No. 6,146,424 or U.S. Pat. No. 5,290,313. Alternatively, an angled adapter element is placed fixedly between the distal end of the pin and the proximal end of the stem, as proposed in U.S. Pat. No. 6,162,255 or EP-A-0 853 930.

These two solutions have the drawback of placing the effective area of the offset of the two axes at a significant depth of the tibial medullary canal. The surgeon therefore has to prepare this canal in advance, by removing the bone tissue in an area of the tibia, which is quite fragile. Furthermore, when the offset is implemented, the distribution of the forces produced in the region of this offset area in the centre of the epiphyseal part of the medullary canal deviates from the anatomical behaviour observed in a healthy tibia.

U.S. Pat. No. 6,214,052 discloses a tibial implant with a reversible offset stem. This implant includes an adapter element that links a tibial tray and the stem that can be assembled in two possible configurations. That is, the tibial axis of the stem has to be offset to the right or to the left with respect to the tibial axis associated to the tray. For this purpose, the adapter element includes a proximal aperture in which is housed a protrusion extending from the distal face of the tray, without interposition of a pin of the here above discussed type.

In use, however, the left/right reversibility of the assembling between the tray and the adapter element is provided due to the fact that the respective cross sections of the protrusion and of the aperture are oblong, which enables no freedom for adjusting the relative positioning of the two tibial axes, except the freedom for choosing between the two opposed left/right configurations. Consequently, a lot of adapter elements with different respective configurations for the angular offset between their proximal and distal parts are necessarily provided for the surgeon, which results in problems of costs, logistics and efficiency.

BRIEF SUMMARY OF THE INVENTION

The present invention relates to an offset stem tibial implant for implanting on a prepared surface of a tibia. One or more adapter elements are used to offset the tray relative to a longitudinal axis of the stem. The low profile construction of the present offset stem tibial implant result in the offset located at, or within a few millimetres of, the prepared surface of the tibia. Contrary to the prior art, the illustrated embodiment of the tibial implant substantially distributes forces produced by the offset substantially on, or adjacent to, the prepared surface of the tibia, rather than in the centre of the epiphyseal part of the medullary canal.

In one embodiment, the low-profile offset stem tibial implant includes a tray with a plate that extends transversely around a first tibial axis. The plate includes a distal surface adapted to engage against the prepared surface of the tibia. An engagement portion extends away from the distal surface of the plate substantially along the first tibial axis. A stem is provided with a distal end adapted to be introduced into the medullary canal of the tibia along a second tibial axis and a proximal end. One or more adapter elements are provided with a proximal portion sized to engage with and contain substantially all of the engagement portion of the plate along the first tibial axis. The adapter element also includes a distal portion adapted to engage with the proximal end of the stem along the second tibial axis. The adapter element permits adjustment of the medio-lateral and antero-posterior position of the second tibial axis relative to the first tibial axis. A plurality of indexing features are located at an interface between the plate and the adapter element to secure the tray in at least three discrete locations around the first tibial axis when in an assembled configuration.

The forces produced by an offset at the adapter element between the first and second tibial axes are preferably distributed substantially on, or adjacent to, the prepared surface of the tibia.

In one embodiment, the engagement portion includes an annular aperture sized to receive a locking member. The locking member includes a threaded portion adapted to engage with a complementary threaded portion on the proximal end of the stem. In another embodiment, the engagement portion includes an annular aperture sized to receive the proximal end of the stem.

A threaded portion on the proximal end of the stem is preferably the primary mechanism to secure the stem, adapter element and tray in the assembled configuration. In one embodiment, the threaded portion on the proximal end of the stem is the sole fastener securing the stem, adapter element and tray in the assembled configuration.

The proximal end of the stem preferably extends above the prepared surface of the tibia when implanted in the medullary canal. In another embodiment, the proximal end of the stem extends into the engagement portion of the plate and above the prepared surface of the tibia when implanted in the medullary canal. The plate and the engagement portion preferably have an axial dimension of less than about 15 mm. In another embodiment, the proximal surface of the plate is perpendicular to the first tibial axis. A pad is optionally engaged with a proximal surface of the plate.

The proximal edge of the adapter element preferably contacts the distal surface of the plate. In another embodiment, the proximal edge of the adapter element engages the plate substantially adjacent to the prepared surface of the tibia. The first and second tibial axes are preferably substantially parallel.

The tibial implant preferably includes a plurality of adapter elements, at least two of which include different offsets between the first tibial axis and the second tibial axis. The adapter element optionally includes a proximal aperture with a center axis that is co-linear with a center axis of an aperture extending through the engagement portion on the plate, when in the assembled configuration.

The indexing features preferably secure the plate in a multiplicity of locations around the first tibial axis. In one embodiment, the indexing features are arranged radially around the first tibial axis. The indexing features are preferably arrange with an angular pitch less than 180°. In one embodiment, the indexing features are arrange with an angular pitch of about 15°. The indexing features are optionally notches distributed regularly along a surface of the engagement portion of the plate and ribs formed on the distal surface of the plate.

Certain embodiments are also directed to a modular offset stem tibial implant which is easier to implant in the tibia and which behaves in a more satisfactory manner from an anatomical perspective, as well as providing a great adjusting freedom for its assembling.

In another embodiment, the tibial implant includes a tray which includes a first tibial axis about which the tray extends transversely and which comprises a plate defining a distal surface that is suitable for being pressed fixedly against the upper end of the tibia of a patient and from which a part of the tray directly projects substantially along the first tibial axis; a stem which includes a second tibial axis about and along which at least one proximal part of the stem extends and which comprises a distal part suitable for being introduced into the medullary canal of the tibia; and an adapter element which is suitable for being placed fixedly between the tray and the stem and which comprises proximal and distal parts, able to be respectively assembled to the tray and to the stem, in a respectively centred manner on the first and second tibial axes, with these two axes substantially parallel and possibly offset relative to one another.

The proximal part of the adapter element prefereably includes a proximal aperture for receiving said part of the tray, said part being substantially complementary of this proximal aperture and being suitable for being housed substantially entirely in this proximal aperture when the tray and the adapter element are assembled to one another, and wherein the proximal part of the adapter element is provided with angular indexing features, about the first tibial axis, relative to the tray, these angular indexing features being adapted to adjust, in a discrete manner, the medio-lateral and antero-posterior positioning of the second tibial axis relative to the first tibial axis when said part of the tray is housed in the proximal aperture of the adapter element.

With certain embodiments of the tibial implant, the adapter element, which allows the effective offset between the two tibial axes of the implant, is assembled as closely as possible to the tray, i.e. in the immediate vicinity of the distal surface of the plate of this tray. In other words, in contrast with tibial implants of the prior art, no pin is placed between this plate and the adapter element. Besides, thanks to the angular indexing features of the adapter element, the surgeon is able to adjust, for a given offset value between the first and the second tibial axes, value that is characteristic of the adapter element that is being used, the positioning of the second tibial axis all about the first tibial axis. Thus, without changing the adapter element, the surgeon freely adjusts, in a discrete manner, the relative positioning between the first and second tibial axes in all the horizontal plane, that is to say along both medio-lateral and antero-posterior directions.

When the components of certain embodiment of the implant are assembled to one another and implanted in the region of the tibia, the distal surface of the plate is pressed firmly against the upper end of the tibia, previously prepared, while the adapter element is located in the opening of the epiphyseal end of the tibial medullary canal, the remainder of this canal receiving the stem. As the adapter element is assembled as closely as possible to the plate of the tray, the bone preparation of the medullary canal essentially, even exclusively, relates to the epiphyseal end of this canal, i.e. an area which is easily accessible to the surgeon and having a certain robustness. Furthermore, the distribution of the forces in the region of the epiphyseal end of the tibia provided with the implant, when this bone is stressed, is therefore substantially in accordance with the anatomical observations of a healthy tibia.

According to advantageous features of the implant according to certain embodiments:

the angular position, about the first tibial axis, of the adapter element relative to the tray can be indexed by the angular indexing features with an angular pitch strictly less than 180°, for example with a pitch of 15°;

the angular indexing features comprise notches distributed regularly along the external or internal periphery of a tubular wall of the adapter element, internally defining the proximal aperture; and/or the angular indexing mechanisms have a complementary shape with at least one reference point of the tray, which projects directly from the distal surface of the plate, so as to immobilize in rotation, about the first tibial axis, the adapter element relative to the tray when the aforementioned part of the tray is housed in the proximal aperture.

To facilitate the assembly of the tray and the adapter element, in addition to providing the surgeon with a materialization of the first tibial axis associated with the tray, the aforementioned part of the tray, able to be housed in the proximal aperture, has an essentially annular shape, centred on the first tibial axis.

In practice, to restrict the axial space requirement of the proximal part of the adapter element, while guaranteeing an efficient assembly between this part and the tray, the axial dimension of the part of the tray is less than about 15 mm, preferably about 10 mm.

According to a particularly compact embodiment of the adapter element, the distal part thereof includes a distal aperture for receiving the proximal part of the stem, which distal aperture opens out into the proximal aperture by creating a passage in which the proximal end of the stem is able to be extended as far as the proximal aperture when the stem and the adapter element are assembled to one another.

It will be noted that this arrangement may be considered independently from the specific type of the assembling between the tray and the proximal part of the adapter element.

In particular, this arrangement is really interesting for its compactness and its reliability, even if the adapter element is not assembled in the immediate vicinity of the distal surface of the plate of the tray.

In combination with this compact embodiment, the tibial implant according to certain embodiments comprises a locking element for locking the tray, the stem and the adapter element assembled to one another, which locking element is suitable for being at least partially introduced into the proximal aperture to be coupled to the distal end of the stem. In this manner, solely by manipulating this locking element, the surgeon carries out relative immobilization of the components of the tibial implant which are assembled to one another, this locking element therefore advantageously occupying a space left free in the proximal aperture of the adapter element.

To facilitate the movements of the surgeon, by allowing the surgeon to manipulate the locking element from the proximal side of the tray, the plate of the tray includes a through-aperture, which extends along the first tibial axis and into which the locking element is suitable for being introduced to extend as far as the proximal aperture when the plate and the adapter element are assembled to one another.

According to one advantageous feature of the implant according to certain embodiments, the locking element is provided with structure to for immobilize rotation about the first tibial axis relative to the tray, suitable for cooperating with associated structures provided on the adapter element when the tray and the adapter element are assembled to one another.

BRIEF DESCRIPTIONS OF SEVERAL VIEWS OF THE DRAWING

The illustrated embodiments can be better understood on reading the following description given purely by way of example and made with reference to the drawings, in which.

DETAILED DESCRIPTION OF THE INVENTION

Figure 1:
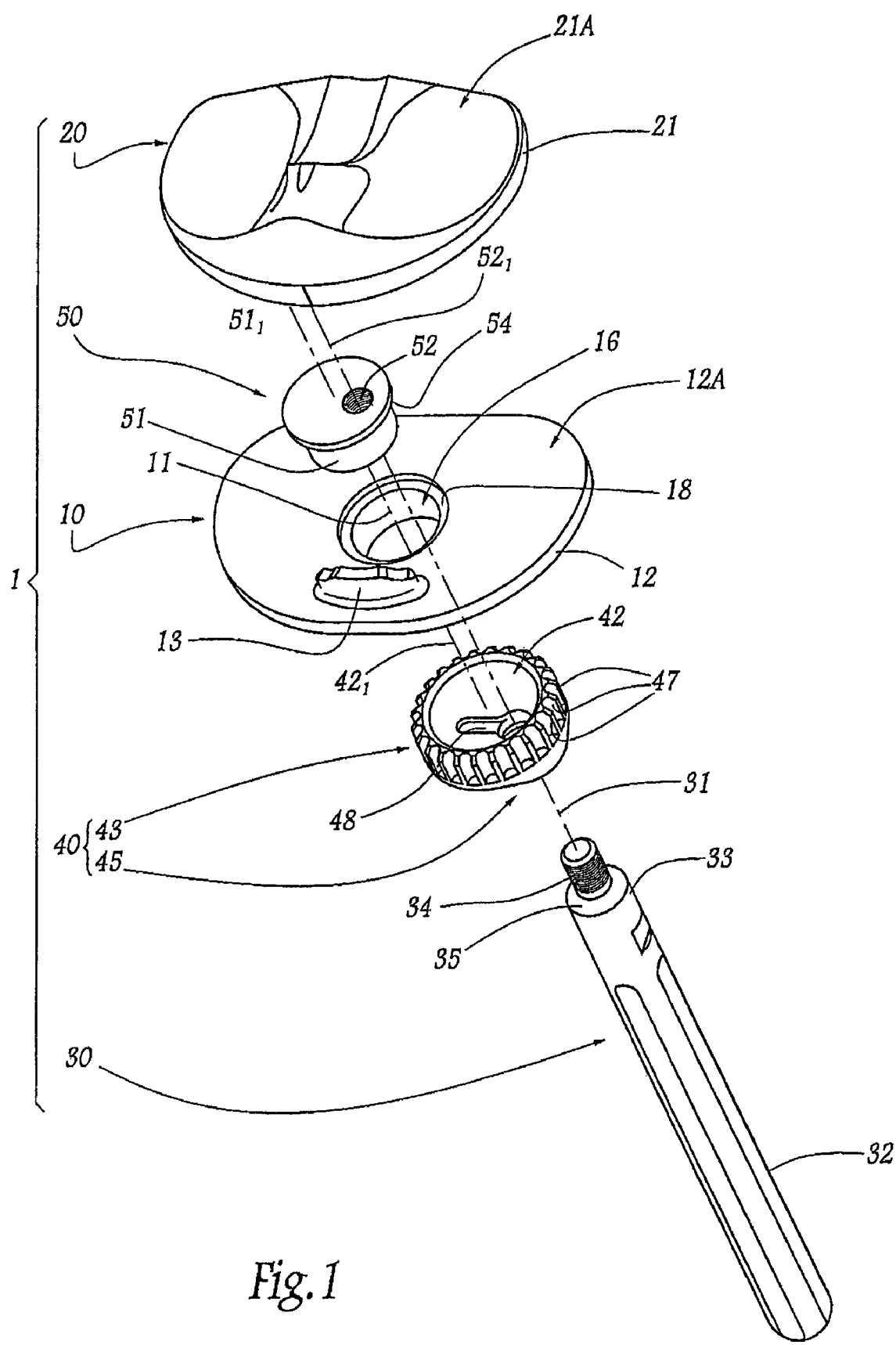
FIG. 1 is an exploded perspective view of an off-set stem tibial implant in accordance with one embodiment of the present invention.
Figure 2:
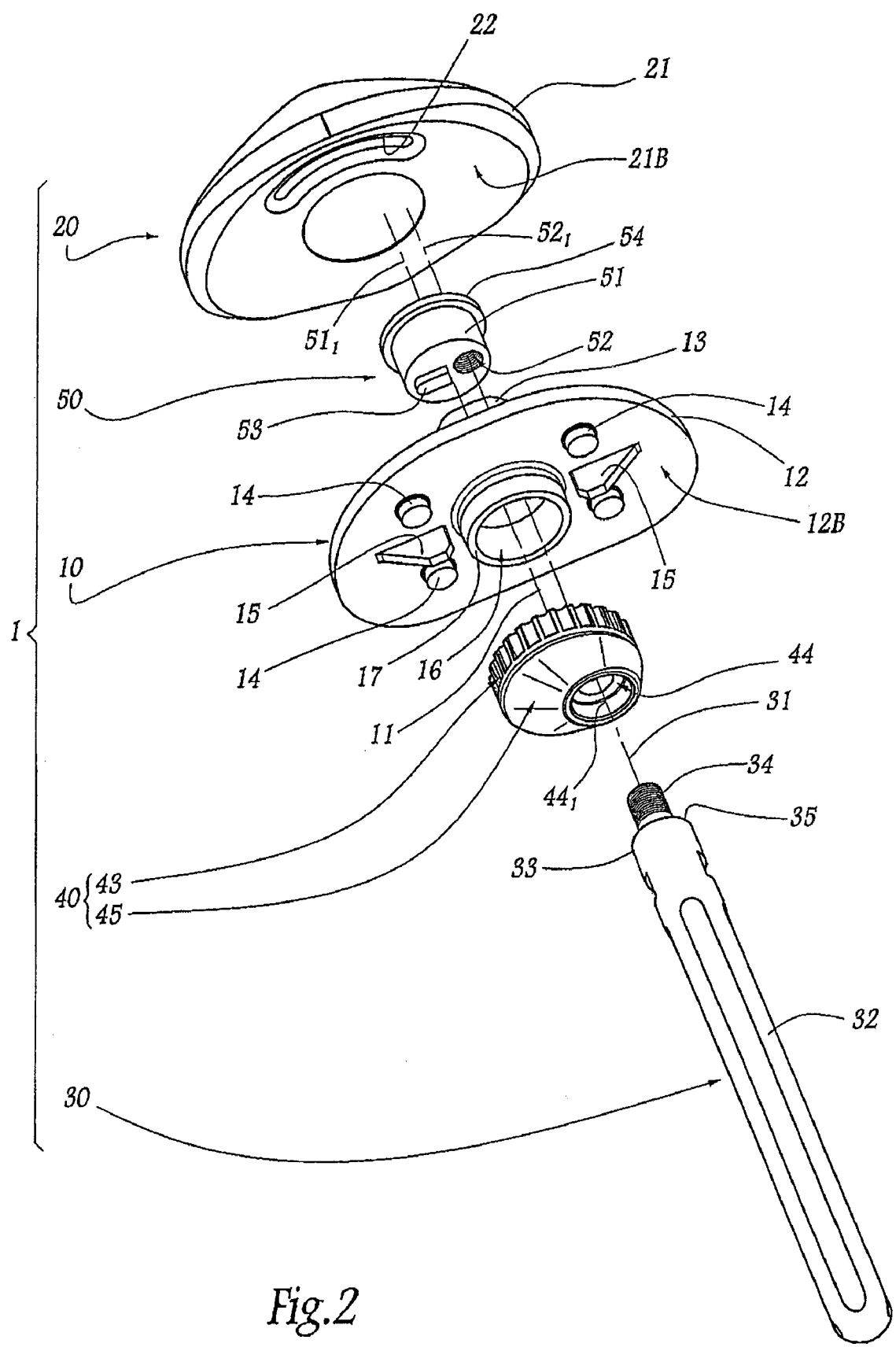
FIG. 2 is an exploded perspective view of the off-set stem tibial implant of FIG. 1 at a different angle.
Figure 3:
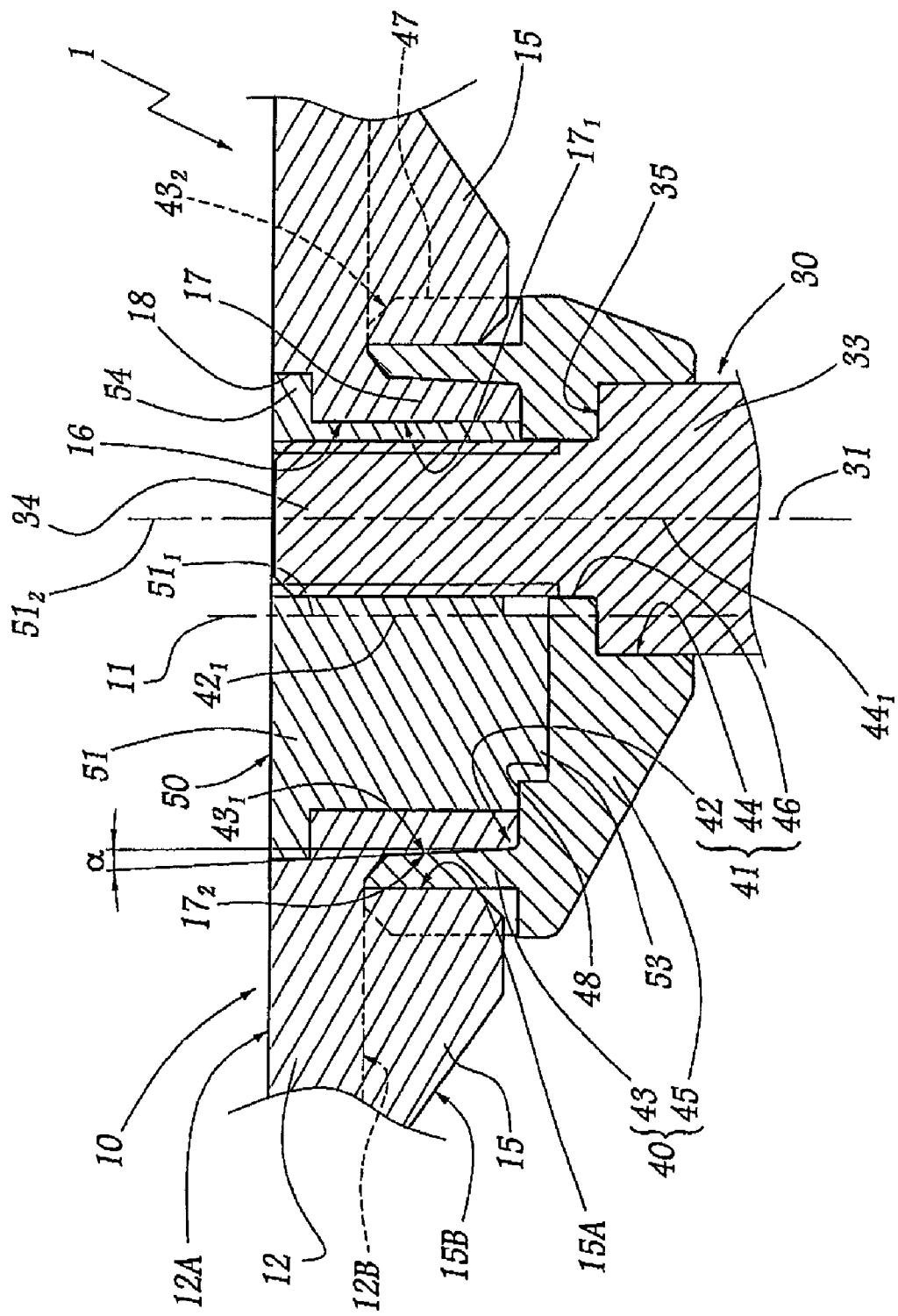
FIG. 3 is a partial longitudinal sectional view of the off-set stem tibial implant of FIGS. 1 and 2.

In FIGS. 1 to 3, a tibial implant 1 is shown forming part of a knee prosthesis of a human being. For convenience, the remainder of the description is oriented relative to the knee of a patient who is standing, such that the term "proximal" denotes a direction directed towards the knee joint while the term "distal" denotes a direction in the opposing direction. Similarly, the terms "upper" and "top" and in contrast, "lower" and "bottom" are understood to be relative to a largely vertical direction in relation to the ground on which the patient is standing, with the tibia thus extending in a substantially vertical manner.

The illustrated embodiment of implant 1 includes five separate components, able to be assembled to one another so that the implant has an assembled configuration allowing its implantation in one piece in the region of the tibia. The illustrated components include a tray 10, a pad 20, a stem 30, an adapter element 40 and a locking element 50, each of which will be discussed in greater detail below.

The tray 10 includes a substantially vertical central axis 1 and comprises a generally planar principal plate 12 that extends in a substantially perpendicular manner to the axis 11, being generally centred on this axis. As shown in FIGS. 1 and 3, the plate 12 thus includes a planar proximal surface 12A against which the distal surface 21B of the body 21 of the pad 20 is provided to be applied and to slide in planar contact/ in one plane.

FIG. 1 illustrates a mobile connection between the tray and the pad is guided by a proximal member 13 projecting, along the axis 11, from the surface 12A of the plate 12, being preferably made in one piece therewith. This member has, in horizontal section, a curved profile substantially centred on the axis 11. When the pad is pressed against the tray, the member 13 is received in an associated slot 22 hollowed out from the distal surface 21B of the body 21, such that the relative movements between the pad and the tray follow a curved trajectory associated with the sliding of the member 13 along the slot 22. Alternatively, the pad 20 can be fixed relative to the surface 12A.

The body 21 of the pad 20 includes a proximal surface 21A defining articulated areas relative to a femoral component, not shown, of the knee prosthesis or of the lower anatomical end of the femur of the patient.

As shown in FIG. 2, the plate 12 includes a planar distal surface 12B intended to be pressed firmly against the upper end of the tibia, previously prepared, for example by resection, so as to form a planar contact. To improve the bone anchoring of the plate 12 against this tibial end, the plate 12 is provided with studs 14 projecting radially, along the axis 11, from the distal surface 12B.

In the illustrated embodiment, the plate 12 is provided with two ribs 15 which project along the axis 11 from respectively the medial and lateral parts of the distal surface 12B. These ribs 15 are preferably substantially symmetrical relative to the axis 11 and are preferably part of a medio-lateral vertical plane corresponding to the sectional plane of FIG. 3.

The ribs 15 preferably include an edge 15A substantially parallel to the axis 11. On the opposing side the ribs 15 include an inclined edge 15B that moves away from the axis 11 in the direction of the plate 12. The inclined, or more generally flared, shape of the edges 15B is preferably dimensioned to be adapted to the epiphyseal opening of the tibial medullary canal, so as to secure the tray 10 in the prepared tibial opening.

The plate 12 includes in its central part penetrated by the axis 11 a through-aperture 16 which, in the illustrated embodiment, is substantially centred on the axis 11. The aperture 16 is preferably cylindrical in shape and is arranged concentric with the axis 11.

On the distal side of the tray 10 annular member 17 extends above the surface 12B along the axis 11. The annular member 17 can be integrally formed from the same material of the tray 10 or can be a separate component. The annular member 17 is substantially centred on the axis 11 and includes a substantially cylindrical internal surface $17_1$, with a circular base also centered on the axis 11. The annular part 17 preferably includes a substantially tapered external surface $17_2$, centered on the axis 11 that converges towards the bottom, with a half angle at the top marked α in FIG. 3.

The stem 30 includes a second tibial axis 31 which, in the illustrated embodiment, corresponds to the longitudinal centre axis of this stem. The stem 30 comprises an externally channelled distal part 32, intended to be introduced into the medullary canal of the tibia, essentially in the region of its diaphyseal part. The stem 30 also comprises a stepped proximal part 33, along the axis 31. More precisely, the part 33 comprises an externally threaded pin 34 at the proximal end that has a diameter less than that of the cylindrical remainder of the part 33 connected to the distal stem part 32. A radial shoulder 35 is located where the pin 34 meets the stem part 33.

The adapter element 40 is adapted to connect, mechanically and in a fixed manner, the tray 10 and the stem 30, so that the tibial axes 11 and 31 are substantially parallel to one another. In the illustrated embodiment, the adapter element radially offsets the tibial axes 11 and 31 by a predetermined value, in practice in the order of several millimetres.

The element 40 includes an aperture 41 which passes through both sides of the element 40 in the direction of the axes 11 and 31. This aperture 41 is made up of a proximal aperture 42, defined by a proximal part 43 of the element 40 and centred on an axis $42_1$, and of a distal aperture 44, defined by a distal part 45 of the element 40 and centred on an axis $44_1$ parallel to the axis $42_1$. A passage 46 centred on the axis $44_1$ connects the distal base of the aperture 42 to the proximal base of the aperture 44. In the illustrated embodiment, the proximal part 43 has a largely tubular shape centred on the axis $42_1$ and internally defining the aperture 42.

In the illustrated embodiment, the aperture 42 is dimensioned to receive, preferably in a complementary manner, the projecting annular part 17 of the tray 10, as shown in FIG. 3. The internal surface $43_1$ of the tubular part 43 preferably has a tapered shape with the axis $42_1$, substantially complementary to the external surface $17_2$ of the annular part 17. The assembly of the tray 10 and the element 40 thus consists in introducing the part 17 into the aperture 42, in a centred manner on the axis 11. In this configuration, as shown in FIG. 3, the axis $42_1$ is thus substantially merged or co-linear with the axis 11.

The distal aperture 44 is itself dimensioned to allow the assembly of the stem 30. The aperture 44 has a cylindrical shape with the axis $44_1$, substantially complementary to the part of the proximal stem 33, while the passage 46 has a substantially complementary section to that of the proximal end of the pin 34. The assembly of the stem 30 with the element 40 consists in introducing the proximal stem part 33 into the inside of the aperture 44, with the pin end 34 received in the passage 46 in a centred manner on the axis 31. In this configuration, as shown in FIG. 3, the axis $44_2$ is now substantially merged or co-linear with the axis 31.

In the illustrated embodiment, the tubular proximal part 43 has a notched external surface $43_2$. A succession of notches 47 are distributed in a substantially uniform manner along its periphery, each notch extending longitudinally in a direction parallel to the axis $42_1$. Each notch 47 is dimensioned to receive, preferably in a substantially complementary manner, the edge 15A of the ribs 15 when the tray 10 and the element 40 are assembled to one another. The radial distance separating two diametrically opposed notches corresponds substantially to the radial distance separating the edges 15A of the two ribs. The transverse section of each notch is preferably U-shaped. In the illustrated embodiment, twenty four notches 47 are distributed uniformly over the external surface $43_2$ such that two successive notches are separated by an angular arc of 15°.

The cooperation of the notches 47 and the ribs 15 allows the angular position of the element 40 to be indexed relative to the tray 10 about the axis 11. When the tray 10 and the element 40 are assembled to one another, a pair of diametrically opposed notches 47 is engaged with the edges 15A of the ribs 15, as shown in FIG. 3, which fixes the angular position of the element 40 about the axis 11. If it is desirable to offset this position at an angle, one of the pairs of opposing notches is used which follows the aforementioned pair along the external periphery of the part 43. Consequently, the angular position of the element 40 relative to the tray 10 may be indexed in a discrete manner, such as for example on a pitch of 15°.

In an alternate embodiment, the notches 47 are located on the inner surface of the aperture 42. Corresponding protrusions are preferably formed on the outer surface of the annular member 17. A variety of other configurations are possible to locate indexing elements, such as for example elements 47, 15A, at the interface between the annular member 17 and the adapter element 40.

The corresponding position of the axis $44_1$, (axis 31) when the stem 30 is assembled to the element 40, corresponds to each indexed position of the element 40 relative to the axis 11. The notches 47 enable adjustment in a discrete manner the angular position of the axis 31 all about axis 11. The number of indexed positions depends on the value of the angular pitch of notches 47, such that a pitch value strictly less than 180° implies that adapter element 40 may be indexed in at least three angular positions around the annular part 17, that respectively correspond to at least three different positions along medio-lateral and antero-posterior directions.

The locking element 50 comprises a principal body 51 having a largely cylindrical shape, with a centre axis $51_1$ and substantially complementary to the aperture 16 defined in the tray 10. This body 51 is provided with a tapped through-hole 52 with a longitudinal axis $52_1$, substantially parallel to the axis $51_1$, being offset relative thereto. The hole 52 is suitable for receiving, by screwing, the threaded pin 34 of the proximal stem part 33.

The assembly of the components of the implant 1 is as follows. In a first step, adapter element 40 is interposed between the tray 10 and the stem 30. In practice, the surgeon has access to a plurality of elements 40 having respective radial offsets between the axes $42_1$ and $44_1$ of their proximal 42 and distal 44 apertures. The family of adapter elements 40 typically have a discrete series of standard offset values, such as for example about 1, 2, 3, 4 and 5 mm. Advantageously, an adapter element 40 with zero offset may also be provided in the range of adapter elements 40 available to the surgeon, which amounts to using an adapter element of which the axes $42_1$ and $44_1$ are co-linear.

After having selected the adapter element, the surgeon attaches the adapter element 40 to the distal surface 12B of the plate 12 of the tray 10. The annular part 17 is axially introduced into the proximal aperture 42 while the edges 15A of the ribs 15 are axially introduced into two diametrically opposed notches 47 selected by the surgeon according to the angular positioning desired by the surgeon. The axial engagement between the tray 10 and the element 40 preferably continues until the entire annular part 17, except for functional clearance, is housed in the aperture 42, as shown in FIG. 3. The edge of the proximal end of the tubular part 43 now extends flush with the distal surface 12B, the element 40 being thus assembled as closely as possible to the plate 12. This nested configuration between the annular member 17 and the aperture 42 contributes to the low profile characteristics of the illustrated tibial implant 1.

The axial immobilization of the annular part 17 in the aperture 42 is, at least partially, associated with the cooperation of the tapered surfaces $17_2$ and $43_1$. These surfaces have the tendency to be wedged against one another in the manner of a Morse cone. In practice, this cooperation over an axial dimension of between about 5 and about 10 mm and with a half angle α in the order of about 6° is sufficient to allow a satisfactory assembly in terms of centring and mechanical resistance.

The axial dimension of the annular part 17 is thus advantageously between about 5 and about 15 mm, preferably about 10 mm. As best illustrated in FIG. 3, proximal element 43 of the adaptor element 40 engages the distal surface 12B of the plate 12. The distal surface 12B engages the prepared surface of the tibial. Consequently, the offset provided by the adaptor element 40 is located at, or within a few millimetres of, the prepared surface of the tibia. Additionally, the distal edge of the annular part 17 engaged with the adaptor element 40 within the about 5 to about 15 mm, preferably about 10 mm discussed above. Contrary to the prior art, the low profile embodiment of the tibial implant 1 substantially distributes forces produced by the offset substantially on, or adjacent to, the prepared surface of the tibia, rather than in the centre of the epiphyseal part of the medullary canal.

Before or after the tray is thus attached to the element 40, the proximal end 33 of the stem 30 is axially introduced into the distal aperture 44, in a centred manner on the axis 31, until its shoulder 35 comes into axial abutment against the base of the aperture 44. In this configuration, the pin 34 extends into the passage 46 and into the proximal aperture 42, as shown in FIG. 3. The stem is introduced into the aperture 44 while the locking element 50 is received in the hole 16 of the tray 10 of which the part 17 is already received in the proximal aperture 42. As a result, the axial progression of the stem 30 towards the top requires the screwing of its pin 34 into the tapped hole 52 of the locking element 50.

To facilitate this screwing, the element 50 is preferably immobilized in rotation about its axis $51_1$, in the aperture 16, by engagement between protrusion portion 53 projecting axially towards the bottom from the distal surface of the body 51 and cavity 48 hollowed out from the bottom surface of the proximal aperture 42. When the protrusion portion 53 and the cavity 48 are engaged in one another, the element 50 is prevented from rotating about the axis 11 and the through-hole 52 is aligned coaxially with the passage 46. The surgeon simply introduces the proximal stem 33 successively into the distal aperture 44, the passage 46 and into threaded engagement with the hole 52.

This screwing continues until the element 50 is firmly held on the threaded pin 34, such that the wall of the element 40 separating its proximal 43 and distal 45 parts is clamped between the shoulder 35 of the stem and the distal surface of the body 51, as shown in FIG. 3. Advantageously, the clamping of the element 50 also contributes to the axial immobilization of the tray 10 and the element 40. In the preferred embodiment, the threaded pin 34 on the stem 32 is the sole fastener retaining the tray 10, adapter element 40 and stem 30 in the assembled configuration illustrated in FIG. 3. It will be appreciated that other features of the present tibial implant 1, such as the tapered surfaces $17_2$ and $43_1$ forming the Morse cone also contribute to retaining the components in the assembled configuration.

The body 51 is provided at its proximal end with a peripheral edge 54 radially projecting from the external surface of the body, while a complementary groove 18 is provided along the periphery of the aperture 16 in the region of its proximal opening. When the element 50 is received in the aperture 16, the edge 53 is housed in the groove 18 so as to press the plate 12 axially towards the element 40 when the element 50 is clamped.

Thus, in one single screwing operation of the proximal stem part 33, the surgeon locks the tray 10, the stem 30 and the adapter element 40 in position in an assembly configuration allowing their final implantation in the tibia. The pad 20 is then attached.

Various arrangements and variants of the tibial implant and method described above can also be envisaged. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

By way of example only, the geometry of the pad 20 is not restricted to that shown. Similarly, the mobile pad 20 may be replaced by a fixed pad, able to be carried in a fixed manner on the proximal surface of the tray 10. The number of notches 47 distributed along the periphery of the proximal part 43 of the element 40 may be greater than or less than that considered above. Similarly, these notches may, as a variant, be made on the internal surface of the aperture 42 with the ribs 15 relocated to engage therewith. The distal part 32 of the stem 30 does not necessarily extend into the rectilinear extension of the proximal part 33. The distal part 32 may be curved over its length, the tibial axis 31, relative to which the radial offset is carried out with the tibial axis 11, thus corresponding to the centre axis of the proximal part of the stem.

All patents disclosed herein, including in the Background of the Invention, are hereby incorporated by reference.

What is claimed is:

1. A low-profile offset stem tibial implant for implanting on a prepared surface of a tibia, the tibial implant comprising:
   a tray including a plate that extends transversely around a first tibial axis, the plate comprising a distal surface adapted to engage against the prepared surface of the tibia, and an engagement portion extending away from the distal surface of the plate substantially along the first tibial axis;
   a stem comprising a distal end adapted to be introduced into a medullary canal of the tibia along a second tibial axis, and a proximal end;
   one or more adapter elements comprising a proximal portion sized to engage with and contain substantially all of the engagement portion of the plate along the first tibial axis, and a distal portion adapted to engage with the proximal end of the stem, the proximal end of the stem extending through the adapter element and into the engagement portion of the plate along the second tibial axis when in an assembled configuration, the adapter element permitting adjustment of the medio-lateral and antero-posterior position of the second tibial axis relative to the first tibial axis; and
   a plurality of indexing features located at an interface between the plate and the adapter element to secure the tray in at least three discrete locations around the first tibial axis when in the assembled configuration.

2. The tibial implant of claim 1 wherein the engagement portion comprises an annular aperture sized to receive a locking member, the locking member comprising a threaded portion adapted to engage with a complementary threaded portion on the proximal end of the stem.

3. The tibial implant of claim 1 wherein the engagement portion comprises an annular aperture sized to receive the proximal end of the stem.

4. The tibial implant of claim 1 wherein a threaded portion on the proximal end of the stem comprises the primary mechanism to secure the stem, adapter element and tray in the assembled configuration.

5. The tibial implant of claim 1 wherein a threaded portion on the proximal end of the stem comprises the sole fastener securing the stem, adapter element and tray in the assembled configuration.

6. The tibial implant of claim 1 wherein the proximal end of the stem extends above the prepared surface of the tibia when implanted in the medullary canal.

7. The tibial implant of claim 1 wherein the proximal end of the stem extends into the engagement portion of the plate and above the prepared surface of the tibia when implanted in the medullary canal.

8. The tibial implant of claim 1 wherein the tray comprises a generally annular shape centered on the first tibial axis.

9. The tibial implant of claim 1 wherein the plate and the engagement portion comprises an axial dimension of less than about 15 mm.

10. The tibial implant of claim 1 wherein a proximal surface of the plate is perpendicular to the first tibial axis.

11. The tibial implant of claim 1 comprising a pad adapted to engage with a proximal surface of the plate.

12. The tibial implant of claim 1 wherein the proximal end of the stem is located along the second tibial axis.

13. The tibial implant of claim 1 wherein a proximal edge of the adapter element engages the plate substantially adjacent to the prepared surface of the tibia.

14. The tibial implant of claim 1 wherein a proximal edge of the adapter element engages the distal surface of the plate generally at the prepared surface of the tibia.

15. The tibial implant of claim 1 wherein the first and second tibial axes are substantially parallel.

16. The tibial implant of claim 1 comprising a plurality of adapter elements, at least two of which comprises different offsets between the first tibial axis and the second tibial axis.

17. The tibial implant of claim 1 comprising first and second adapter elements with different offsets between the first tibial axis and the second tibial axis.

18. The tibial implant of claim 1 wherein the adapter element comprises a proximal aperture with a center axis that is co-linear with a center axis of an aperture extending through the engagement portion on the plate, when in the assembled configuration.

19. The tibial implant of claim 1 wherein the indexing features secure the plate in a multiplicity of locations around the first tibial axis.

20. The tibial implant of claim 1 wherein the indexing features are arranged radially around the first tibial axis.

21. The tibial implant of claim 1 wherein the indexing features are arranged with an angular pitch less than 180°.

22. The tibial implant of claim 1 wherein the indexing features are arranged with an angular pitch of about 15°.

23. The tibial implant of claim 1 wherein forces produced by an offset at the adapter element between the first and second tibial axes are distributed substantially on, or adjacent to, the prepared surface of the tibia.

24. A low-profile offset stem tibial implant for implanting on a prepared surface of a tibia, the tibial implant comprising:
   a tray including a plate that extends transversely around a first tibial axis, the plate comprising a distal surface adapted to engage against the prepared surface of the tibia, and an engagement portion extending away from the distal surface of the plate substantially along the first tibial axis;
   a stem comprising a distal end adapted to be introduced into a medullary canal of the tibia along a second tibial axis, and a proximal end;
   one or more adapter elements comprising a proximal portion adapted to substantially nest with the engagement portion of the plate along the first tibial axis, and a distal portion adapted to engage with the proximal end of the stem the proximal end of the stem extending through the adapter element and into the engagement portion of the plate along the second tibial axis when in an assembled configuration, the adapter element permitting adjustment of the medio-lateral and antero-posterior position of the second tibial axis relative to the first tibial axis; and
   a plurality of indexing features located at an interface between the plate and the adapter element adapted to secure the tray in at least three discrete locations around the first tibial axis when in the assembled configuration.

25. A low-profile offset stem tibial implant for implanting on a prepared surface of a tibia, the tibial implant comprising:
   a tray including a plate that extends transversely around a first tibial axis, the plate comprising a distal surface adapted to engage against the prepared surface of the tibia, and an engagement portion extending away from the distal surface of the plate substantially along the first tibial axis;
   a stem comprising a distal end adapted to be introduced into a medullary canal of the tibia along a second tibial axis, and a proximal end;
   one or more adapter elements comprising a proximal portion adapted to substantially engage with the engagement portion of the plate along the first tibial axis, and a distal portion adapted to engage with the proximal end of the stem, the proximal end of the stem extending through the adapter element and into the engagement portion of the plate along the second tibial axis when in an assembled configuration, and the adapter element permitting adjustment of the medio-lateral and antero-posterior position of the second tibial axis relative to the first tibial axis, such that the tibial implant substantially distributes forces produced by an offset between the first and second tibial axes at the adapter element substantially on, or adjacent to, the prepared surface of the tibia; and
   a plurality of indexing features located at an interface between the plate and the adapter element adapted to secure the tray in a plurality of discrete locations around the first tibial axis when in the assembled configuration.

26. A low-profile offset stem tibial implant for implanting on a prepared surface of a tibia, the tibial implant comprising:
   a tray including a plate that extends transversely around a first tibial axis, the plate comprising a distal surface adapted to engage against the prepared surface of the tibia, and an engagement portion extending away from the distal surface of the plate substantially along the first tibial axis;
   a stem comprising a distal end adapted to be introduced into a medullary canal of the tibia along a second tibial axis, and a proximal end;
   one or more adapter elements comprising a proximal portion sized to accept the engagement portion of the plate along the first tibial axis, and a distal portion adapted to engage with the proximal end of the stem, the adapter element and tray being directly secured to the stem along the second tibial axis in an assembled configuration such that the medio-lateral and antero-posterior position of the second tibial axis relative to the first tibial axis is adjustable by the adapter element; and
   a plurality of indexing features located at an interface between the plate and the adapter element to secure the tray in a plurality of discrete locations around the first tibial axis when in the assembled configuration.

27. The tibial implant of claim 26, further comprising a locking member having a threaded portion adapted to engage with a complementary threaded portion on the proximal end of the stem to secure the adapter element and the tray to the stem.

28. The tibial implant of claim 27 wherein the locking member includes a protrusion portion for engaging a notch in the proximal portion of the adapter when in the assembled configuration.

29. The tibial implant of claim 26 wherein the tray is adjustable relative to the stem when the stem is positioned in the medullary canal of the tibia.

30. The tibial implant of claim 26 wherein the medio-lateral and antero-posterior position of the second tibial axis are adjustable relative to the first tibial axis when the stem is positioned in the medullary canal of the tibia.

31. A low-profile offset stem tibial implant for implanting on a prepared surface of a tibia, the tibial implant comprising:
- a tray including a plate that extends transversely around a first tibial axis, the plate comprising a distal surface adapted to engage against the prepared surface of the tibia, an engagement portion extending away from the distal surface of the plate substantially along the first tibial axis, and an aperture extending from a proximal surface of the tray into the engagement portion;
- a stem comprising a distal end adapted to be introduced into a medullary canal of the tibia along a second tibial axis, and a proximal end;
- one or more adapter elements comprising a proximal portion sized to accept the engagement portion along the first tibial axis, and a distal portion adapted to engage with the proximal end of the stem, such that the medio-lateral and antero-posterior position of the second tibial axis relative to the first tibial axis is adjustable by the adapter element;
- a plurality of indexing features located at an interface between the plate and the adapter element to secure the tray in a plurality of discrete locations around the first tibial axis when in the assembled configuration; and
- a locking member positioned in the aperture from the proximal surface of the tray to secure the tray and the adapter element to the proximal end of the stem.

32. The tibial implant of claim 31 wherein the adapter element engages the engagement portion in a nested configuration.

33. The tibial implant of claim 31 wherein the locking member comprises a threaded portion adapted to engage with a complementary threaded portion on the proximal end of the stem.

34. The tibial implant of claim 31 wherein the tray is adjustable relative to the stem when the stem is positioned in the medullary canal of the tibia.

35. The tibial implant of claim 31 wherein the medio-lateral and antero-posterior position of the second tibial axis are adjustable relative to the first tibial axis when the stem is positioned in the medullary canal of the tibia.

* * * * *